(12) United States Patent
Hanada et al.

(10) Patent No.: US 6,740,362 B2
(45) Date of Patent: *May 25, 2004

(54) FLUORINATED CARRIER SOLVENT

(75) Inventors: Tsuyoshi Hanada, Ichihara (JP); Masaaki Tsuzaki, Ichihara (JP)

(73) Assignee: Asahi Glass Company, Limited, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 10/292,596

(22) Filed: Nov. 13, 2002

(65) Prior Publication Data

US 2003/0077392 A1 Apr. 24, 2003

Related U.S. Application Data

(62) Division of application No. 10/119,690, filed on Apr. 11, 2002, now Pat. No. 6,544,595, which is a division of application No. 09/755,129, filed on Jan. 8, 2001, now abandoned.

(30) Foreign Application Priority Data

Jan. 11, 2000 (JP) ........................................ 2000-002783

(51) Int. Cl.$^7$ .............................. B05D 3/00; B05D 5/00; C23G 5/028
(52) U.S. Cl. ................................ 427/393.5; 427/385.5; 427/387; 252/182.15; 252/364; 252/58; 252/54; 510/412
(58) Field of Search ........................... 252/364, 182.12, 252/182.13, 182.15, 58, 54; 510/175, 199, 245, 408, 412, 177; 524/462; 427/387, 393.5, 385.5

(56) References Cited

U.S. PATENT DOCUMENTS

| 5,346,645 A | 9/1994 | Omure et al. |
| 5,531,916 A | 7/1996 | Merchant |
| 5,648,325 A | 7/1997 | Kitamura et al. |
| 5,667,594 A | 9/1997 | Omure et al. |
| 5,973,055 A | 10/1999 | Michaud et al. ............ 524/462 |

FOREIGN PATENT DOCUMENTS

| EP | 0 863 194 | 9/1998 |
| EP | 0 885 952 | 12/1998 |
| EP | 0 924 245 | 6/1999 |
| WO | WO 99/36485 | 7/1999 |
| WO | WO 99/63043 | 12/1999 |
| WO | WO 00/17301 | 3/2000 |

Primary Examiner—Joseph D. Anthony
(74) Attorney, Agent, or Firm—Oblon, Spivak, McClelland, Maier & Neustadt, P.C.

(57) ABSTRACT

A method for mixing an organic chemical substance with a carrier solvent, wherein the carrier solvent comprises at least one fluorinated solvent A selected from the group consisting of (perfluorohexyloxy)methane and tridecafluorohexane.

14 Claims, No Drawings

FLUORINATED CARRIER SOLVENT

This application is a divisional of Ser. No. 10/119,690 filed Apr. 11, 2002 now U.S. Pat. No. 6,544,595 which is a divisional of Ser. No. 09/755,129 filed Jan. 8, 2001 now abandoned.

The present invention relates to a carrier solvent comprising (perfluorohexyloxy)methane and/or tridecafluorohexane, which is useful as a carrier solvent for various organic chemical substances such as a lubricant, a coating material, a mold release agent, a water/oil repellent, an oil or a grease.

Heretofore, as carrier solvents for various organic chemical substances, trichlorotrifluoroethane (hereinafter referred to as R113), dichloropentafluoropropane (hereinafter referred to as R225) and perfluorocarbons (hereinafter referred to as PFC) such as perfluorohexane, which are excellent in non-flamability and chemical and thermal stability, have been widely used.

However, they respectively have adverse effects on the global environment, such that R113 and R225 have an ozone-depletion potential, and PFC has a very high global warming potential. Production of chlorofluorocarbons such as R113 has already been prohibited, and in developed countries, hydrochlorofluorocarbons such as R225 are phase out by 2020. Further, PFC is listed as a substance subject to regulation by the Kyoto Protocol for preventing global warming. It is an object of the present invention to provide a carrier solvent which has a performance equal to such R113, R225 or PFC and which has little adverse effect on the global environment.

As a result of extensive studies, the present inventors have found that a fluorinated solvent comprising, as an effective component, a fluorinated solvent (hereinafter referred to as a fluorinated solvent A) selected from the group consisting of (perfluorohexyloxy)methane and tridecafluorohexane, can be used as a carrier solvent.

Namely, the present invention provides a method for dissolving an organic chemical substance with a carrier solvent, wherein the carrier solvent comprises at least one fluorinated solvent A selected from the group consisting of (perfluorohexyloxy)methane and tridecafluorohexane.

Further, the present invention provides a composition comprising an organic chemical substance and at least one fluorinated solvent A selected from the group consisting of (perfluorohexyloxy)methane and tridecafluorohexane.

In the present invention, the (perfluorohexyloxy)methane means a compound represented by the molecular formula $C_6F_{13}OCH_3$, and is particularly preferably a compound represented by the rational formula $CF_3(CF_2)_5OCH_3$. Further, in the present invention, the tridecafluorohexane means a compound represented by the molecular formula $C_6F_{13}H$ and is preferably 1,1,1,2,2,3,3,4,4,5,5,6,6,-tridecafluorohexane i.e. $CF_3(CF_2)_5H$. $C_6F_{13}OCH_3$ and $C_6F_{13}H$ may be used alone or in admixture. Further, $C_6F_{13}OCH_3$ and $C_6F_{13}H$ may respectively be used alone or may be used in combination as a mixture of two or more of them.

To the carrier solvent of the present invention comprising the fluorinated solvent A as an effective component, various other components may be incorporated depending upon various purposes. For example, in order to increase the solubility or in order to adjust the evaporation rate, an organic solvent (hereinafter referred to as an organic solvent B) other than those described above may further be incorporated.

As a preferred example of such an organic solvent B, at least one member selected from the group consisting of hydrocarbons, alcohols, ketones, halogenated hydrocarbons (provided that tridecafluorohexane is excluded), ethers (provided that (perfluorohexyloxy)methane is excluded) and esters, may be mentioned. The proportion of the organic solvent B, based on the total amount of the organic solvent B and the fluorinated solvent A, is usually at most 40% by mass, the same applies hereinafter, preferably at most 20%, further preferably at most 10%. In a case where the carrier solvent of the present invention has an azeotropic composition, it is preferred to use it in the form of such an azeotropic composition.

The hydrocarbons are preferably ones having carbon number five to fifteen. For example, n-pentane, 2-methylbutane, n-hexane, 2-methylpentane, 2,2-dimethylbutane, 2,3-dimethylbutane, n-heptane, 2-methylhexane, 3-methylhexane, 2,4-dimethylpentane, n-octane, 2-methylheptane, 3-methylheptane, 4-methylheptane, 2,2-dimethylhexane, 2,5-dimethylhexane, 3,3-dimethylhexane, 2-methyl-3-ethylpentane, 3-methyl-3-ethylpentane, 2,3,3-trimethylpentane, 2,3,4-trimethylpentane, 2,2,3-trimethylpentane, 2-methylheptane, 2,2,4-trimethylpentane, n-nonane, 2,2,5-trimethylhexane, n-decane, n-dodecane, 1-pentene, 2-pentene, 1-hexene, 1-octene, 1-nonene, 1-decene, cyclopentane, methylcyclopentane, cyclohexane, methylcyclohexane, ethylcyclohexane, bicyclohexane, cyclohexene, α-pinene, dipentene, decalin, tetralin and amyl naphthalene may be mentioned. More preferably, n-pentane, cyclopentane, n-hexane, cyclohexane or n-heptane may, for example, be mentioned.

The alcohols are preferably ones having carbon number one to sixteen. For example, methanol, ethanol, n-propyl alcohol, isopropyl alcohol, n-butyl alcohol, sec-butyl alcohol, isobutyl alcohol, tert-butyl alcohol, 1-pentanol, 2-pentanol, 1-ethyl-1-propanol, 2-methyl-1-butanol, 3-methyl-1-butanol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 3,5,5-trimethyl-1-hexanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol, 4-methylcyclohexanol, α-terpineol, 2,6-dimethyl-4-heptanol, nonylalcohol and tetradecylalcohol, may be mentioned. More preferably, methanol, ethanol or isopropylalcohol may, for example, be mentioned.

The ketones are preferably ones having carbon number three to nine. Specifically, acetone, methyl ethyl ketone, 2-pentanone, 3-pentanone, 2-hexanone, methyl isobutyl ketone, 2-heptanone, 3-heptanone, 4-heptanone, diisobutyl ketone, mesityl oxide, pholone, 2-octanone, cyclohexanone, methylcyclohexanone, isopholone, 2,4-pentanedione, 2,5-hexanedione, diacetone alcohol and acetophenone may, for example, be mentioned. More preferably, acetone or methyl ethyl ketone may, for example be mentioned.

The halogenated hydrocarbons are preferably ones having carbon number one to five. For example, dichloromethane, 1,1-dichloroethane, 1,2-dichloroethane, 1,1,2-trichloroethane, 1,1,1,2-tetrachloroethane, 1,1,2,2-tetrachloroethane, pentachloroethane, 1,1-dichloroethylene, 1,2-dichloroethylene, trichloroethylene, tetrachloroethylene, 1,2-dichloropropane, dichloropentafluoropropane, dichlorofluoroethane and decafluoropentane may be mentioned. More preferably, dichloromethane, trichloroethylene or tetrachloroethylene may, for example, be mentioned.

The ethers are preferably ones having carbon number two to eight. For example, diethyl ether, dipropyl ether, diisopropyl ether, dibutyl ether, ethyl vinyl ether, butyl vinyl ether, anisole, phenetole, methyl anisole, dioxane, furan, methyl furan and tetrahydrofuran may be mentioned. More preferably, diethyl ether, diisopropyl ether dioxane or tetrahydrofuran may, for example, be mentioned.

The esters are preferably ones having carbon number two to nineteen. Specifically, methyl formate, ethyl formate, propyl formate, butyl formate, isobutyl formate, pentyl formate, methyl acetate, ethyl acetate, propyl acetate, isopropyl acetate, butyl acetate, isobutyl acetate, sec-butyl acetate, pentyl acetate, methoxybutyl acetate, sec-hexyl acetate, 2-ethylbutyl acetate, 2-ethylhexyl acetate, cyclohexyl acetate, benzyl acetate, methyl propionate, ethyl propionate, butyl propionate, methyl butyrate, ethyl butyrate, butyl butyrate, isobutyl isobutyrate, ethyl 2-hydroxy-2-methylpropionate, methyl benzoate, ethyl benzoate, propyl benzoate, butyl benzoate, benzyl benzoate, γ-butyrolactone, diethyl oxalate, dibutyl oxalate, dipentyl oxalate, diethyl malonate, dimethyl maleate, diethyl maleate, dibutyl maleate, dibutyl tartarate, tributyl citrate, dibutyl sebacate, dimethyl phthalate, diethyl phthalate and dibutyl phthalate may, for example, be mentioned. More preferably, methyl acetate or ethyl acetate may, for example, be mentioned.

As the organic chemical substance to be dissolved by the carrier solvent in the present invention, various organic chemical substances may be mentioned, such as a lubricant, a coating agent, a mold release agent, a water/oil repellent, a moisture-proof coating agent, a water-proof agent, a glazing agent, an antistatic agent, an oil and a grease. The organic chemical substance is preferably a lubricant. In the composition of the present invention, the amount of the organic chemical substance in the carrier solvent is preferably from 0.01 to 50%, more preferably from 0.05 to 30%, most preferably from 0.1 to 20%.

As the substance coated with the composition of the present invention, various materials may be mentioned, such as a metal, a synthetic resin, a glass, and a ceramic. A preferred substance in the present invention is a metal or a synthetic resin.

In the manufacture of various products, the organic chemical substance such as a lubricant dissolved by the carrier solvent in the present invention, can be coated at predetermined portions of such products. After the coating, the carrier solvent is evaporated.

Now, the present invention will be described in further detail with reference to Examples. However, it should be understood that the present invention is by no means restricted to such specific Examples.

EXAMPLES 1 TO 14

A fluorinated oil having a perfluoroalkyl group (the amount of the fluorinated oil in the carrier solvent was 2%) was dissolved into $CF_3(CF_2)_5OCH_3$ (hereinafter referred to as PFHOM) or $CF_3(CF_2)_5H$ (hereinafter referred to as TDFH), or a carrier solvent containing it as an effective component, as shown in the following Table 1, and the surface of a vacuum evaporated aluminum layer on a plate made of iron was coated by this mixture, and the carrier solvent evaporated in air to form a lubricant layer on the surface of the plate. The drying property of the carrier solvent at that time and the state of the obtained coating layer were visually observed. Evaluation of the state of the coating layer was represented by ⊚: good coating layer, ○: substantially good, Δ: partial irregularities observed, and X: substantial irregularities observed. Further, evaluation of the drying property was represented by ⊚: immediately dried, ○: dried within 10 minutes, Δ: dried within one hour, and X: not dried within one hour. The results are shown in Table 1. The number in brackets ( ) indicates the blend ratio.

TABLE 1

| Example | Carrier solvent | State of coating layer | Drying property |
|---|---|---|---|
| 1 | PFHOM (100) | ⊚ | ⊚ |
| 2 | PFHOM (95)/n-heptane (5) | ⊚ | ⊚ |
| 3 | PFHOM (95)/ethanol (5) | ⊚ | ⊚ |
| 4 | PFHOM (95)/acetone (5) | ⊚ | ⊚ |
| 5 | PFHOM (90)/dichloromethane (10) | ⊚ | ⊚ |
| 6 | PFHOM (95)/diethyl ether (5) | ⊚ | ⊚ |
| 7 | PFHOM (99)/ethyl acetate (1) | ⊚ | ⊚ |
| 8 | TDFH (100) | ⊚ | ⊚ |
| 9 | TDFH (95)/n-heptane (5) | ⊚ | ⊚ |
| 10 | TDFH (95)/ethanol (5) | ⊚ | ⊚ |
| 11 | TDFH (95)acetone (5) | ⊚ | ⊚ |
| 12 | TDFH (90)/dichloromethane (10) | ⊚ | ⊚ |
| 13 | TDFH (95)/diethyl ether (5) | ⊚ | ⊚ |
| 14 | TDFH (99)/ethyl acetate (1) | ⊚ | ⊚ |

EXAMPLES 15 TO 28

A silicone oil comprising a polyalkylsiloxane (the amount of the silicone oil in the carrier solvent was 2%) was dissolved into a carrier solvent shown in the following Table 2, and the surface of the stainless steel plate was coated by this mixture, and the carrier solvent evaporated in air to form the silicone oil layer on the surface of the stainless steel plate. The drying property of the carrier solvent at that time and the state of the obtained coating layer was visually observed.

Evaluation of the state of the coating layer was represented by ⊚: good coating layer, ○: substantially good, Δ: partial irregularities observed, and X: substantial irregularities observed. Further, evaluation of the drying property was represented by ⊚: immediately dried, ○: dried within 10 minutes, Δ: dried within one hour, and X: not dried within one hour. The results are shown in Table 2. The number in brackets ( ) indicates the blend ratio.

TABLE 2

| Example | Carrier solvent | State of coating layer | Drying property |
|---|---|---|---|
| 15 | PFHOM (100) | ⊚ | ⊚ |
| 16 | PFHOM (95)/n-heptane (5) | ⊚ | ⊚ |
| 17 | PFHOM (95)/ethanol (5) | ⊚ | ⊚ |
| 18 | PFHOM (95)/acetone (5) | ⊚ | ⊚ |
| 19 | PFHOM (90)/dichloromethane (10) | ⊚ | ⊚ |
| 20 | PFHOM (95)/diethyl ether (5) | ⊚ | ⊚ |
| 21 | PFHOM (99)/ethyl acetate (1) | ⊚ | ⊚ |
| 22 | TDFH (100) | ⊚ | ⊚ |
| 23 | TDFH (95)/n-heptane (5) | ⊚ | ⊚ |
| 24 | TDFH (95)/ethanol (5) | ⊚ | ⊚ |
| 25 | TDFH (95)acetone (5) | ⊚ | ⊚ |
| 26 | TDFH (90)/dichloromethane (10) | ⊚ | ⊚ |
| 27 | TDFH (95)/diethyl ether (5) | ⊚ | ⊚ |
| 28 | TDFH (99)/ethyl acetate (1) | ⊚ | ⊚ |

EXAMPLES 29 TO 34

A test coupon made of an acrylic resin or a polycarbonate resin was immersed in PFHOM or TDFH, or a solvent containing it as an effective component, shown in the following Table 3 at room temperature for 24 hours and then taken out, whereupon the changes of the appearance of the resins were observed. Evaluation of the appearance was represented by ⊚: no change, Δ: slight cloud or dissolution observed, and X: cloud, cracking or dissolution observed. The results are shown in Table 3. the number in brackets () indicates the blend mass ratio.

EXAMPLE 35 (COMPARATIVE EXAMPLE)

Using R225, the same tests as in Examples 29 to 34 were carried out, and the changes of the appearance of the resins were observed. The results are shown in Table 3.

TABLE 3

| Example | Carrier solvent | Acrylic resin | Poly-carbonate resin |
|---------|-----------------|---------------|----------------------|
| 29 | PFHOM (100) | ⊚ | ⊚ |
| 30 | PFHOM (95)/n-heptane (5) | ⊚ | ⊚ |
| 31 | PFHOM (95)/ethanol (5) | ⊚ | ⊚ |
| 32 | TDFH (100) | ⊚ | ⊚ |
| 33 | TDFH (95)/n-heptane (5) | ⊚ | ⊚ |
| 34 | TDFH (95)/ethanol (5) | ⊚ | ⊚ |
| 35 | R225 (100) | X | X |

As is evident from Examples, the carrier solvents of the present invention are excellent in the dissolving property and drying property, and no irregularities of the coated layers are observed. Further, they have a proper solvency similar to R113, R225 and PFC which used to be used, and they are useful for treatment of composite parts made of metal, plastic, elastomer, etc. without presenting any adverse effects.

The entire disclosure of Japanese Patent Application No. 2000-002783 filed on Jan. 11, 2000 including specification, claims and summary are incorporated herein by reference in its entirety.

What is claimed is:

1. A method for coating a substrate, comprising
contacting a substrate with a liquid composition comprising a silicon oil, a co-solvent and a carrier solvent, and
evaporating the carrier solvent and the co-solvent to form a substrate coated with the silicon oil,
wherein the carrier solvent is (perfluorohexyloxy)methane, tridecafluorohexane, or both, and the co-solvent is at least one of an alcohol, a hydrocarbon, an ether, an ester, or a ketone, and is present in an amount that does not affect the appearance of the substrate, and
wherein the substrate is a polycarbonate resin substrate or an acrylic resin substrate.

2. The method of claim 1, wherein the carrier solvent is (perfluorohexyloxy)methane.

3. The method of claim 1, wherein the carrier solvent is tridecafluorohexane.

4. The method of claim 1, wherein the co-solvent is selected from the group consisting of n-heptane, acetone, ethylacetate, diethyether and diethylether.

5. The method of claim 1, wherein the silicon oil is a polyalkylsiloxane.

6. The method of claim 1, wherein the silicon oil is present in an amount of from 0.01 to 50% by mass of the composition.

7. The method of claim 1, wherein the silicon oil is present in an amount of 0.1 to 20% by mass of the composition.

8. The method of claim 1, wherein the composition is contacted with a portion of the substrate.

9. The method of claim 1, wherein the composition further comprises a fluorinated oil.

10. The method of claim 9, wherein the fluorinated oil has a perfluoroalkyl group.

11. The method of claim 1, wherein contacting includes spraying the composition on the substrate.

12. The method of claim 1, wherein evaporating is carried out in air.

13. The method of claim 1, wherein the co-solvent is present in an amount of at most 40% of the total weight of the carrier solvent.

14. The method of claim 1, wherein the co-solvent is present in an amount of 1 to 10% of the total weight of the carrier solvent.

* * * * *